United States Patent [19]

Greiner et al.

[11] Patent Number: 5,246,953
[45] Date of Patent: Sep. 21, 1993

[54] PROCESS FOR PROTECTING PLANT PROPAGATION PRODUCTS AND THE PLANTS OBTAINED FROM THEM

[75] Inventors: Alfred Greiner, St Cyr Au Mont d'Or; Jean Hutt, Lyons; Jacques Mugnier, La Balme de Sillingy; Regis Pepin, Rilleux la Pape, all of France

[73] Assignee: Rhone-Poulenc Secteur Agrochimie, Lyons, France

[21] Appl. No.: 714,254

[22] Filed: Jun. 12, 1991

[30] Foreign Application Priority Data

Jun. 12, 1990 [FR] France .................................. 90 07551

[51] Int. Cl.$^5$ ............................................. A01N 43/64
[52] U.S. Cl. .................................................. 514/383
[58] Field of Search ..................................... 514/383

[56] References Cited

FOREIGN PATENT DOCUMENTS 378953 7/1990 European Pat. Off. .

OTHER PUBLICATIONS

Hutt et al, C.A. vol. 114, 81835y (1991).
Fine Chemicals Directory Search System entry for 2,2-dimethylcyclopentanone (1990).

Primary Examiner—Allen J. Robinson
Attorney, Agent, or Firm—Morgan & Finnegan

[57] ABSTRACT

Process for protecting, by curative or preventive means, plant propagation products and the plants obtained from them.

The invention relates to a process for protecting, by curative or preventive means, plant propagation products and the plants obtained from them against fungal diseases, wherein there is applied to the said propagation product a fungicide composition containing 2-(4-chlorobenzylidene)-5,5-dimethyl-1-(1H-1,2,4-triazol-1-ylmethyl)-1-cyclopentanol, an agriculturally suitable inert carrier and an agriculturally suitable surface-active agent.

It also relates to plant propagation products coated with the fungicide composition and to the said fungicide composition.

17 Claims, No Drawings

PROCESS FOR PROTECTING PLANT PROPAGATION PRODUCTS AND THE PLANTS OBTAINED FROM THEM

The present invention relates to a process for protecting, by curative or preventive means, plant propagation products and the plants obtained from them against fungal diseases by applying to the propagation product a fungicide composition comprising an active material 2-(4-chlorobenzylidene)-5,5-dimethyl-1-(1H-1,2,4-triazol-1-ylmethyl)-1-cyclopentanol, an agriculturally suitable inert carrier and optionally an agriculturally suitable surface-active agent. The present invention also relates to a propagation product coated with the said fungicide composition and, finally, to a fungicide composition intended especially for implementing the protection process according to the invention.

Indeed, it has been found, in a completely unexpected manner, that the said fungicide composition, in addition to its fungicide activity when applied to the propagation products, allows protection of the crop after germination and possibly up to harvest and its main industrial usefulness is to avoid, in numerous cases, one or more foliar treatments.

2-(4-Chlorobenzylidene)-5,5-dimethyl-1-(1H-1,2,4-triazol-1-ylmethyl)-1-cyclopentanol is described in the European Patent Application No. 89/420520 filed on 27 Dec. 1989 and unpublished to date.

The compound 2-(4-chlorobenzylidene)-5,5-dimethyl-1-(1H-1,2,4-triazol-1-ylmethyl)-1-cyclopentanol may be obtained in the following manner:

100 ml of a 10% aqueous solution of sodium hydroxide were added to a mixture of 10 g of 2,2-dimethylcyclopentanone and 13.8 g of 4-chlorobenzaldehyde in 100 ml of ethanol at 0° C. After 30 minutes, a thick slurry was filtered off and the solid was washed and then dried. 12.5 g of 2,2-dimethyl-5-(4-chlorobenzylidene)-1-cyclopentanone with a melting point of 120° C. were obtained. This compound, dissolved in 50 ml of THF, was added to a solution formed in the following manner: 1.9 g of sodium hydroxide (80% dispersion in mineral oil) in 50 ml of anhydrous DMSO were heated to 80° C. until complete dissolution of the solid. The solution was then diluted with 100 ml of THF, then cooled to −10° C. A solution of 11.5 g of trimethylsulphonium iodide in 80 ml of dimethyl sulphoxide was added to the mixture in the course of ten minutes and the mixture was stirred for 15 minutes at −10° C. A solution of 11.8 g of 2,2-dimethyl-4-chloro-5-(4-chlorobenzylidene)-1-cyclopentanone was then added in 100 ml of THF.

The mixture thus obtained was left at room temperature then poured into water and extracted with ether, washed with water, dried and distilled. 7-(4-chlorobenzylidene)-4,4-dimethyl-1-oxaspiro[2.4]heptane, which was directly used in the subsequent stage, was obtained.

A mixture of 5 g of product with 2.8 g of 1,2,4-triazole and 11 g of potassium carbonate was heated in 40 ml of N,N-dimethylformamide for 4 hours. The mixture was poured into water and extracted with ethyl acetate. The organic phase was washed, dried and recrystallized to yield the stated product whose melting point is 143° C.

The fungicide 2-(4-chlorobenzylidene)-5,5-dimethyl-1-(1H-1,2,4-triazol-1-ylmethyl)-1-cyclopentanol is represented by the formula:

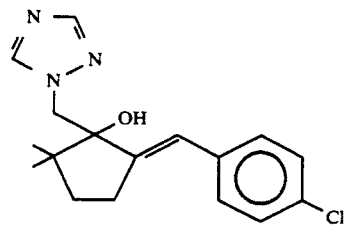

The structure of the compound is, in a very large majority of cases (>95%), that in which the para-chlorophenyl group is in the E position with respect to the carbon bearing the hydroxyl group.

2,2-Dimethylcyclopentanone may be obtained in a manner which is known in the literature or is available commercially (see Fine Chemical Directory).

In Examples 14, 15 and 16 of the European Patent Application No. 89/420520, there is described a wheat seed of the Talent variety coated with the said triazole.

The term "propagation product" is meant to designate all the generative parts of the plant which may be used for its propagation. Included are, for example, seeds (in the narrow sense), roots, fruits, tubers, bulbs, rhizomes and plant sections. Sprouted plants and young plants which have to be transplanted after germination or after coming out of the soil are also included. These young plants may be protected before transplanting by a total or partial treatment by steeping.

Seeds are preferred for crops other than potatoes.

The following are preferred among the propagation products suitable for the treatment process according to the invention:

dicotyledon seeds: pea, cucumber, melon, soybean, cotton, sunflower, rape, bean, flax and beet;

monocotyledon seeds: cereals, including wheat (with the exception of the Talent variety before the onset of tillering), barley, rye and oat, maize and rice; and potato tubers.

Preferably, the seeds are coated with 0.1 to 500 g of active material per quintal of seed, preferably 1 to 400 g per quintal.

Preferably, in the case of tubers, they are coated with a quantity of active material which corresponds to soaking the said product in a composition containing 0.1 g/l to 100 g/l of active material.

The compositions according to the invention normally contain between 0.5 and 95% active material.

The term "carrier", in the present text, designates an organic or inorganic material, natural or synthetic, with which the active material is combined in order to facilitate its application to the plant, to seeds or the soil. This carrier is therefore generally inert and must be agriculturally acceptable, in particular on the treated plant. The carrier may be solid (clays, natural or synthetic silicates, silica, resins, waxes, solid fertilizers, and the like) or liquid (water, alcohols, ketones, petroleum fractions, aromatic or paraffinic hydrocarbons, chlorinated hydrocarbons, liquefied gases, and the like).

The surface-active agent may be an emulsifying, dispersing or wetting agent of the ionic or nonionic type. The following may be mentioned by way of example: polyacrylic acid salts, lignosulphonic acid salts, phenolsulphonic or naphthalenesulphonic acid salts, polycondensates of ethylene oxide and fatty alcohols or fatty acids or fatty amines, substituted phenols (alkylphenols or arylphenols in particular), ester salts of sulphosuccinic acids, taurine derivatives (alkyltaurates in particular), phosphoric esters of alcohols or of polyoxyethylated phenols. The presence of at least one surface-active agent is often required given that the active material and/or the inert carrier are insoluble in water and that the vector agent of the application is water.

These compositions may also contain other ingredients such as, for example, protective colloids, adhesives, thickeners, thixotropic agents, penetrating agents, stabilizers, sequestrants, pigments, colorants and polymers.

More generally, the compositions according to the invention may be combined with all those solid or liquid additives found in the usual formulation procedures for applying the seed treatment in particular.

In this regard, it will be noted that in the jargon used by those skilled in the art, the term seed treatment in fact refers to the treatment of grains.

The methods of application are well known to those skilled in the art and they may be used without risk within the scope of the present invention. The methods of application include, for example, the formation of a thin film or coating.

Among the compositions, solid or liquid compositions may generally be mentioned.

By way of solid composition forms, the following may be mentioned: powders for dusting or dispersing (with a content of compound of formula (I) which may be as high as 100%) and granules, in particular those obtained by extrusion, by compaction, by impregnation of a granulated carrier and by granulation from a powder (the content of compound of formula (I) in these granules being between 1 and 80% in the latter cases).

The compositions may further be used in the form of a powder for dusting; a composition comprising 50 g of active material, 10 g of finely divided silica, 10 g of organic pigment and 970 g of talc may thus be used; these consultants are mixed and ground and the mixture is applied by dusting.

By way of liquid composition forms or forms intended to constitute liquid compositions on application, the following may be mentioned: solutions, in particular water-soluble concentrates, emulsifiable concentrates, emulsions, concentrated suspensions, aerosols, wettable powders (or spray powder), pastes and dispersible granules.

The emulsifiable or soluble concentrates most often compare 10 to 80% of active material, the emulsions or solutions ready for application contain, for their part, 0.01 to 20% of active material.

For example, in addition to the solvent, the emulsifiable concentrates may contain, when necessary, 2 to 20% of appropriate additives such as stabilizers, surface-active agents, penetrating agents, corrosion inhibitors, colorants or adhesives previously mentioned.

From these concentrates, emulsions of any desired concentration, which are particularly suitable for application to seeds, may be obtained by dilution with water.

The concentrated suspensions, which can also be applied by spraying, are prepared so as to obtain a stable fluid product which does not form deposits, and they normally contain from 10 to 75% of active material, 0.5 to 15% of surface-active agents, 0.1 to 10% of thixotropic agents, 0 to 10% of appropriate additives, such as pigments, colorants, antifoams, corrosion inhibitors, stabilizers, penetrating agents and adhesives and, by way of carrier, water or an organic liquid in which the active material is barely soluble or insoluble: some organic solid materials or inorganic salts may be dissolved in the carrier to help prevent sedimentation or as antifreeze for water.

The wettable powders (or spray powder) are normally prepared so that they contain 20 to 95% of active material, and they normally contain, in addition to the solid carrier, from 0 to 5% of a wetting agent, 3 to 10% of a dispersing agent and, when necessary, from 0 to 10% of one or more stabilizers and/or other additives, such as pigments, colorants, penetrating agents, adhesives, or anticoagulating agents, and the like.

To obtain these spray powders or wettable powders, the active material is thoroughly mixed in appropriate mixers with the additional substances and they are ground using mills or other appropriate grinders. Spray powders are thereby obtained whose wettability and ability to form suspensions are advantageous; they can be suspended in water at any desired concentration and these suspensions may be used very advantageously in particular for application to seeds.

In place of the wettable powders, pastes may be prepared. The conditions and methods for the preparation and the use of these pastes are similar to those for wettable powders or spray powders.

The dispersible granules are normally prepared by agglomeration, in appropriate granulation systems, of the compositions of the wettable powder type.

As already indicated, the dispersions and aqueous emulsions, for example the compositions obtained by diluting a wettable powder or an emulsifiable concentrate according to the invention with water, are included within the general scope of the present invention. The emulsions may be of the water-in-oil or oil-in-water type and they may have a thick consistency like that of a "mayonnaise".

Among these compositions, those skilled in the art will advantageously choose that or those which is/are suitable in relation to the conditions of use.

According to a preferred variant, the composition according to the invention will furthermore contain a pigment known per se to reduce the phytotoxicity of triazoles. This variant may be useful in the case of high fungicide doses, especially for dicotyledons.

In the case of rice, it has been found that the composition also possessed a disinfectant effect.

The process according to the invention may be used in a preventive as well as curative capacity for the protection of plant propagation products against fungi, particularly of the basidiomycete, ascomycete, adelomycete or imperfect fungi types, in particular rusts, bunt, oidium, eyespot, fusarioses, fusarium roseum, fusarium nivale, net blotch, leaf blotch, septoria spot, rhizoctonioses of vegetables and plants in general and, in particular, of cereals such as wheat, barley, rye, oat and their hybrids and also rice and maize.

The process according to the invention allows in particular the combating of fungi particularly of the following types: basidiomycetes, ascomycetes, adelomycetes or imperfect fungi such as *Botrytis cinerea, Erysiphe graminis, Puccinia graminis, Puccinia recondita, Piricularia oryzae, Cercospora beticola, Puccinia striiformis, Erysiphe cichoracearum, Rhinchosporium secalis, Fusarium, Solani, Fusarium oxysporum* (melonis, for example), *Pyrenophora avenae, Septoria tritici, Septoria avenae, Whetzelinia sclerotiorum, Mycosphaerella fijiensis, Alternaria solani, Aspergillus niger, Cercospora arachidicola, Cladosporium herbarum, Tilletia caries, Tilletia contreversa, Fusarium roseum, Fusarium nivale, Helmin-* thosporium oryzae, Helminthosporium teres, Helminthosporium gramineum, Helminthosporium sativum, Penicillium expansum, Pestalozzia sp, Phoma betae, Phoma foveate, Phoma lingam, Ustilago maydis, Ustilago nuda, Ustilago hordei, Ustilago avenae, Verticillium dahliae, Ascochyta pisi, Guignardia bidwellii, Corticium rolfsii, Phomopsis viticola, Sclerotinia sclerotiorum, Sclerotinia minor, Coryneum cardinale, Rhizoctonia solani, Acrostalagmus koningi, Alternaria, Colletotrichum, Diplodia natalensis, Gaeumannomyces graminis, Gibberella fujikuroi, Hormodendron cladosporioides, Myrothecium verrucaria, Paecylomyces varioti, Pellicularia sasaki, Phellinus megaloporus, Sclerotium rolfsii, Stachybotris atra, Trichoderma pseudokoningi, Trichothecium roseum.

The process makes it possible to effectively combat cereal diseases (oidium, rust, eyespot, leaf blotch, net blotch, septoria spot and fusarioses). They are also of great interest because of their activity on grey mould (Botrytis) and leaf spot, and, as a result, they can be applied to products of crop propagation as varied as vines, market garden crops, arboricultural crops and tropical crops such as groundnuts, banana plants, coffee plants, pecan nuts and the like.

These compositions are also useful for the disinfection of cereal seeds against Ustilago nuda, Septoria nodorum, Tilletia caries and Tilletia controversa, Hemin thosporium gramineum and numerous Fusarium species.

The subject of the invention is also the plant propagation product with preferred variants such as defined above coated with and/or containing 2-(4-chlorobenzylidene)-5,5-dimethyl-1-(1H-1,2,4-triazol-1-ylmethyl)-1-cyclopentanol on the condition that the said propagation product is not a wheat grain of the Talent variety.

The term coated with and/or containing implies that the active material is mainly present at the surface of the product during application although a more or less substantial portion may penetrate the product depending on the mode of application. When the said propagation product is replanted, it absorbs the active material.

In fact, commercially, it could be said that most of the active material is at the surface most of the time.

Preferably, the propagation product is selected from the group consisting of:

dicotyledons: pea, cucumber, soybean, melon, cotton, sunflower, rape, bean, flax and beet monocotyledons: soft winter wheat with the exception of the Talent variety, soft spring wheat, hard wheat, barley, rye, oat, lucerne, maize and rice.

Preferably, the seeds are coated with an amount of 0.1 to 500 g of active material per quintal of seed and preferably 1 to 400 g/quintal.

Another advantageous variant consists in that the propagation product is a potato tuber preferably coated with a quantity of active material which corresponds to soaking the said product in a solution containing 0.1 g/l to 100 g/l of active material.

The invention also relates to a fungicide composition such as defined in claims 12 to 17 and in the description above, the term especially in claims 12 to 14 implying that the composition is also claimed independently of the destination.

On the other hand, the term exclusively implies in claims 15 to 17 that the indication (implementation of the process) is a characteristic of the invention.

The invention also relates to a fungicide composition intended especially for implementing the process according to the invention, with the exception of wheat of the Talent variety, containing 2-(4-chlorobenzylidene)-5,5-dimethyl-1-(1H-1,2,4-triazol-1-ylmethyl)-1-cyclopentanol, an agriculturally suitable inert carrier and optionally an agriculturally suitable surface-active agent.

Preferably, the fungicide composition is characterised in that the propagation products are seeds chosen from among the seeds of:

dicotyledons: pea, cucumber, soybean, melon, cotton, sunflower, rape, bean, flax and beet monocotyledons: soft winter wheat with the exception of wheat of the Talent variety, hard wheat, soft spring wheat, barley, rye, maize and rice.

Preferably, the fungicide composition is characterised in that it contains 0.5 to 95% of active material.

The invention also relates to a fungicide composition intended exclusively for implementing the process according to the invention, characterised in that it applies to seeds of soft winter wheat and in that it contains 2-(4-chlorobenzylidene)-5,5-dimethyl-1-(1H-1,2,4-triazol-1-ylmethyl)-1-cyclopentanol, an agriculturally suitable inert carrier and optionally an agriculturally suitable surface-active agent.

The fungicide composition is characterised in particular in that it applies to seeds of the Talent variety.

Preferably, the fungicide composition is characterized in that it contains 0.5 to 95% of active material.

The invention is further illustrated by the examples given below, which are not intended to limit the invention.

EXAMPLE 1

2-(4-Chlorophenylbenzylidene)-5,5-dimethyl-1-(1H-1,2,4-triazol-1-ylmethyl)-1-cyclopentanol (A) has been formulated in the form of a concentrated suspension at 200 g/l according to techniques well known to those skilled in the art.

Wheat seeds of the Nebraska variety particularly sensitive to yellow rust (*Puccinia striiformis*) are treated with the above formulation after appropriate dilution so as to obtain the quantities of active material per quintal indicated in the table below. These seeds are sown. The results are read 192 days after sowing.

| Treatment | Dose g/q | % foliar surface attacked |
|---|---|---|
| Control | — | 42.5 |
| A | 30 | 18.8 |
| | 60 | 11.0 |
| | 90 | 9.3 |
| | 120 | 3.0 |

EXAMPLE 2: PHYTOTOXICITY TRIAL

Barley seeds are treated as before and one month after sowing, the percentage of sprouted seeds is determined.

The results are shown below.

| Treatment | Dose g/q | % of sprouted seeds |
|---|---|---|
| Control | — | 78.5 |
| A | 60 | 76.1 |
| | 120 | 76.3 |
| | 180 | 77.5 |

No sign of phytotoxicity was observed.

EXAMPLE 3

Barley seeds naturally contaminated by *Ustilago nuda* treated with the above information so as to obtain the quantities of active material per quintal indicated in the table below. These seeds are sown.

The results are read 8 months after sowing.

| Treatment | Dose g/q | Ears attacked/m² |
|---|---|---|
| Control | — | 30.3 |
| A | 5 | 0 |
|  | 10 | 0 |
|  | 30 | 0 |

EXAMPLE 4

Barley seeds naturally contaminated by *Septoria nodorum* are treated as in Example 2.

The results are read 1 months after sowing.

| Treatment | Dose g/q | % efficacy |
|---|---|---|
| Control | — | 0 |
| A | 5 | 100 |
|  | 10 | 100 |
|  | 30 | 100 |

EXAMPLE 5

Barley seeds are treated as in Example 4.

The results are read 152 days after sowing, after an attack by *Erysiphe graminis*.

| Treatment | Dose g/q | % foliar surface attacked |
|---|---|---|
| Control | — | 35.0 |
| A | 30 | 18.8 |
|  | 60 | 11.3 |
|  | 90 | 9.0 |
|  | 120 | 9.3 |

EXAMPLE 6

Maize seeds naturally contaminated by *Gibberella fujikuroi* are treated with the slurry of Example 1.

The results are read 22 days after sowing.

| Treatment | Dose g/q | % of healthy plants, 22 days after sowing |
|---|---|---|
| Control | — | 13.5 |
| A | 5 | 24.1 |
|  | 25 | 26.2 |
|  | 50 | 59.0 |
|  | 100 | 70.2 |

EXAMPLE 7

Rice seeds naturally contaminated by *Gibberella fujikuroi* (Fusarium) are treated with the slurry of Example 1.

The results are read one months after sowing.

| Treatment | Dose g/q | % diseased plants |
|---|---|---|
| Control | — | 98.9 |
| A | 5 | 45.6 |
|  | 25 | 3.0 |

-continued

| Treatment | Dose g/q | % diseased plants |
|---|---|---|
|  | 100 | 0 |

No phytotoxic effect was observed.

EXAMPLE 8

Pea seeds naturally contaminated by *Fusarium solani* are treated with the slurry of Example 1.

The results are read one months after sowing.

| Treatment | Dose g/q | % stalks attacked |
|---|---|---|
| Control | — | 57.3 |
| A | 5 | 27.1 |
|  | 25 | 23.2 |
|  | 50 | 22.1 |
|  | 100 | 10.0 |

EXAMPLE 9

Cucumber seeds are treated with the slurry of Example 1.

The results are read two months after sowing, after an attack by *Erysiphe cichoriacearum*.

| Treatment | Dose g/q | % foliar surface attacked |
|---|---|---|
| Control | — | 36.2 |
| A | 25 | 23.8 |
|  | 50 | 19.7 |
|  | 100 | 18.3 |
|  | 200 | 6.6 |

EXAMPLE 10

Melon seeds are treated with the slurry of Example 1.

The results are read 14 days after a contamination by *fusarium oxysporum var-melonis*.

| Treatment | Dose g/q | % efficacy |
|---|---|---|
| Control | — | 0 |
| A | 3 | 100 |
|  | 6 | 100 |
|  | 12 | 100 |
|  | 25 | 100 |

EXAMPLE 11

Potato tubers naturally contaminated by *Phoma foveata* are soaked in a slurry as indicated in Example 1.

The results are read 64 days after sowing.

| Treatment | Dose g a.m/l | % diseased tuber, 64 d. after sowing |
|---|---|---|
| Control | — | 84.8 |
| A | 1 | 4.4 |
|  | 5 | 2.0 |
|  | 10 | 2.0 |

It has moreover been found that the current fungicide is selective, with no sign of phytotoxicity on seeds of:

| | | |
|---|---|---|
| | cotton | at 100 g/q |
| | sunflower | at 50 g/q |
| dicots. | rape | at 50 g/q |
| | bean | at 25 g/q |

-continued

| | flax | at 10 g/q |
| | beet | at 50 g/q |
| monocots. | maize | at 200 g/q | under the same conditions as before.

Similarly, it has been found that the fungicide exhibited an excellent activity, in seed treatment, against:

| Phoma betae | beet |
| Phoma | potato |
| Vascular Fusarioses | melon |
| Aschochyta (anthracnose) | pea |

Finally it has been found that the fungicide composition was also useful in soil treatment for rice and banana plants.

SOIL TREATMENT

BANANA PLANTS—LEAF SPOT

Table. Effect of A against *Mycosphaerella musicola*, applied in soil treatment to banana plants in Ivory Coast.

The banana plants are treated at all stages of development.

| Treatment | Dose/banana plant (g) | % leaves attacked |
|---|---|---|
| Control | — | 26 |
| A | 0.5 | 6 |

We claim:

1. A process for protecting, by curative or preventive means, plant propagation products selected from the group consisting of seeds, roots, fruits, tubers, bulbs, rhizomes, plant sections, sprouted plants and young plants and the plants obtained from them against fungal diseases, which comprises applying to the propagation product a fungicidal composition comprising an active material 2-(4-chlorobenzylidene)-5,5-dimethyl-1-(1H-1,2,4-triazol-1-ylmethyl)-1-cyclopentanol, an agriculturally suitable inert carrier and optionally an agriculturally suitable surface active agent, in such a way that 0.1 to 500 g of the active material per quintal of plant propagation product is applied when coating, or 0.1 to 100 g of the active material per liter of the composition is applied to the plant propagation product when soaking or steeping.

2. The process according to claim 1, wherein the propagation product is a seed.

3. The process according to claim 2, wherein the seed is a monocotyledon seed.

4. The process according to claim 3, wherein the seed is selected from the group consisting of hard wheat, soft spring wheat, soft winter wheat, barley, oat, rye, maize and rice.

5. The process according to claim 2, wherein the seed is a dicotyledon seed.

6. The process according to claim 5, wherein the seed is selected from the group consisting of pea, cucumber, melon, cotton, sunflower, rape, soybean, bean, flax and beet.

7. The process according to claim 1, wherein the propagation product is a potato tuber.

8. The process according to claim 2, wherein 1 to 400 g of the active material per quintal of seed is applied.

9. A plant propagation product selected from the group consisting of seeds, roots, fruits, tubers, bulbs, rhizomes, plant sections, sprouted plants and young plants, with the exception of wheat grains of the Talent variety, coated with and/or containing therein a fungicidal composition comprising an active material 2-(4-chlorobenzylidene)-5,5-di-methyl-1-(1H-1,2,4-triazol-1-ylmethyl)-1-cyclopentanol, an agriculturally suitable inert carrier and optionally an agriculturally suitable surface-active agent, in such a way that 0.1 to 500 g of the active material per quintal of plant propagation product is applied when coating, or 0.1 to 100 g of the active material per liter of the composition is applied to the plant propagation product when soaking or steeping.

10. The plant propagation product according to claim 9, wherein the product is a seed.

11. The plant propagation product according to claim 10, wherein the seed is a dicotyledon seed.

12. The plant propagation product according to claim 11, wherein the seed is selected from the group consisting of pea, cucumber, soybean, melon, cotton, sunflower, rape, bean, flax and beet.

13. The plant propagation product according to claim 10, wherein the seed is a monocotyledon seed.

14. The plant propagation product according to claim 13, wherein the seed is selected from the group consisting of soft winter wheat with the exception of the Talent variety, hard wheat, soft spring wheat, barely, rye, maize and rice.

15. The propagation product according to claim 10, wherein the seed is coated with 1 to 400 g of the active material per quintal of seed.

16. The propagation product according to claim 9, wherein the product is a potato tuber.

17. A fungicidal composition comprising an active material 2-(4-chlorobenzylidene)-5,5-dimethyl-1-(1H-1,2,4-triazol-1-ylmethyl)-1-cyclopentanol, an agriculturally suitable inert carrier and optionally an agriculturally suitable surface-active agent, wherein the composition contains 0.5 to 95% of the active material.

* * * * *